(12) United States Patent
Coste-Maniere et al.

(10) Patent No.: US 7,607,440 B2
(45) Date of Patent: Oct. 27, 2009

(54) METHODS AND APPARATUS FOR SURGICAL PLANNING

(75) Inventors: Eve C. Coste-Maniere, Sophia Antipolis Cedex (FR); Louai Adhami, Sophia Antipolis Cedex (FR); Jean-Daniel Boissonnat, Sophia Antipolis Cedex (FR); Alain Carpentier, Paris (FR); Gary S. Guthart, Mountain View, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 864 days.

(21) Appl. No.: 10/165,413

(22) Filed: Jun. 6, 2002

(65) Prior Publication Data

US 2003/0109780 A1    Jun. 12, 2003

Related U.S. Application Data

(60) Provisional application No. 60/296,808, filed on Jun. 7, 2001.

(51) Int. Cl.
*A61B 19/00* (2006.01)
(52) U.S. Cl. .................. 128/898; 600/407; 600/427
(58) Field of Classification Search ............ 600/407, 600/416, 424, 426, 427; 700/245; 128/922
See application file for complete search history.

(56) References Cited

U.S. PATENT DOCUMENTS

| | | | | |
|---|---|---|---|---|
| 5,205,289 A | * | 4/1993 | Hardy et al. ............. | 600/429 |
| 5,279,309 A | * | 1/1994 | Taylor et al. ............ | 600/595 |
| 5,445,166 A | | 8/1995 | Taylor | |
| 5,572,999 A | * | 11/1996 | Funda et al. ............ | 600/118 |
| 5,791,908 A | | 8/1998 | Gillio | |
| 5,871,018 A | | 2/1999 | Delp et al. | |
| 6,244,809 B1 | * | 6/2001 | Wang et al. ............. | 414/1 |
| 6,390,097 B1 | * | 5/2002 | Chandra ................. | 128/898 |
| 6,505,065 B1 | * | 1/2003 | Yanof et al. ............. | 600/427 |
| 6,529,765 B1 | * | 3/2003 | Franck et al. ........... | 600/427 |
| 6,786,896 B1 | * | 9/2004 | Madhani et al. ......... | 606/1 |

OTHER PUBLICATIONS

Chiu et al. 3-D Image Guidance for Minimally Invasive Robotic Coronary Artery Bypass. Jun. 8, 2000. The Heart Surgery Forum. 3 (3). pp. 224-231.*

(Continued)

*Primary Examiner*—Brian Casler
*Assistant Examiner*—James Kish

(57) ABSTRACT

Methods and apparatus for enhancing surgical planning provide enhanced planning of entry port placement and/or robot position for laparoscopic, robotic, and other minimally invasive surgery. Various embodiments may be used in robotic surgery systems to identify advantageous entry ports for multiple robotic surgical tools into a patient to access a surgical site. Generally, data such as imaging data is processed and used to create a model of a surgical site, which can then be used to select advantageous entry port sites for two or more surgical tools based on multiple criteria. Advantageous robot positioning may also be determined, based on the entry port locations and other factors. Validation and simulation may then be provided to ensure feasibility of the selected port placements and/or robot positions. Such methods, apparatus, and systems may also be used in non-surgical contexts, such as for robotic port placement in munitions diffusion or hazardous waste handling.

29 Claims, 10 Drawing Sheets

OTHER PUBLICATIONS

Tabaie et al. Endoscopic Coronary Artery Bypass Graft (ECABG) Procedure with Robotic Assistance. Sep. 7, 1999. The Heart Surgery Forum. 2 (4). pp. 310-317.*

Hanna et al. Optimal Port Locations For Endoscopic Intracorporeal Knotting. 1997. Surgical Endoscopy. vol. 11. pp. 397-401.*

Adhami et al, Planning and Simulation of Robotically Assisted Minimal Invasive Surgery, Oct. 11-14, 2000., MICCAI '00.*

Minor et al., A Dexterous Manipulator For Minimally Invasive Surgery, May 1999, IEEE, International Conference on Robotics & Automation, pp. 2057-2064.*

Austad, A., et al., *Computer aided planning of trocar placement and robot settings in robot assisted surgery* CARS 2001—H.U. Lemke at al., Eds., Elsevier Science B.V. (© 2001) pp. 981-986.

L. Adhami, E. Coste-Maniere, and J.-D. Boissonnat. *Planning and simulation of robotically assisted minimal invasive surgery*. In Proceedings MICCAI, vol. 1935 of Lecture Notes in Computer Science. Springer, Oct. 2000, 11 pages total.

Ève Coste-Maniere, Louaï Adhami, Renaud Severac-Bastide, Kenneth Lobontiu, Adrian Salisbury, Jean-Daniel Boissonnat, Nick Swarup, Gary Guthart, Élie Mousseaux, and Alain Carpentier. *Optimized port placement for the totally endoscopic coronary artery bypass grafting using the da Vinci robotic system*. In D. Russ and S. Singh, editors, Lecture Notes in Control and Information Sciences, Experimental Robotics VII, vol. 271. Springer, 2001, 10 pages total.

J. S. Rotnes, J. Kaasa, G. Westgaard, E. M. Eriksen, P. Ø. Hvidsten, K. Strøm, V. Sørhus, Y. Halbwachs, E. Haug, M. Grimnes, H. Fontenelle, T. Ekeberg, J. B. Thomassen, O. J. Elle, E. Fosse. *A tutorial platform suitable for surgical simulator training (SimMentor(TM))*. Medicine Meets Virtual Reality (MMVR) 2002, J.D. Westwood et al. (eds.), IOS Press, 2002, 4 pages total, Feb. 13, 2002.

Jan Sigurd Rotnes, Johannes Kaasa, Geir Westgaard, Eivind Myrold Eriksen, Per Øyvind Hvidsten, Kyrre Strøm, Vidar Sørhus, Yvon Halbwachs, Ole Jakob Elle, and Erik Fosse *Digital trainer developed for robotic assisted cardiac surgery* Presented at MMVR2001, 4 pages total.

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

\* cited by examiner

METHODS AND APPARATUS FOR SURGICAL PLANNING

CROSS-REFERENCES TO RELATED APPLICATIONS

This non-provisional application claims the benefit of priority from U.S. Provisional Patent Application Ser. No. 60/296,808, filed Jun. 7, 2001, the full disclosure of which is incorporated herein by reference.

BACKGROUND OF THE INVENTION

The present invention generally relates to methods and apparatus for enhancing surgical planning. More specifically, the invention relates to methods and apparatus for planning, validating and simulating port placement for minimally invasive surgery, such as laparoscopic and/or robotic surgery.

Minimally invasive surgical techniques generally reduce the amount of extraneous tissue damage during surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. Patient recovery times, patient discomfort, surgical side effects, and time away from work can also be reduced through the use of minimally invasive surgery.

In theory, a significant number of surgical procedures could be performed by minimally invasive techniques to achieve the advantages just described. Only a small percentage of procedures currently use minimally invasive techniques, however, because certain methods, apparatus and systems are not currently available in a form for providing minimally invasive surgery.

Traditional forms of minimally invasive surgery typically include endoscopy, which is visual examination of a hollow space with a viewing instrument called an endoscope. Minimally invasive surgery with endoscopy may be used in many different areas in the human body for many different procedures, such as in laparoscopy, which is visual examination and/or treatment of the abdominal cavity, or in minimally invasive heart surgery, such as coronary artery bypass grafting. In traditional laparoscopic surgery, for example, a patient's abdominal cavity is insufflated with gas and cannula sleeves (or "entry ports") are passed through small incisions in the musculature of the patient's abdomen to provide entry ports through which laparoscopic surgical instruments can be passed in a sealed fashion. Such incisions are typically about ½ inch (about 12 mm) in length.

Minimally invasive surgical instruments generally include an endoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by a long extension tube, typically of about 12 inches (about 300 mm) in length, for example, so as to permit the surgeon to introduce the end effector to the surgical site and to control movement of the end effector relative to the surgical site from outside a patient's body.

To perform a minimally invasive surgical procedure, a surgeon typically passes the working tools or instruments through the entry ports to the internal surgical site and manipulates the instruments from outside the abdomen by sliding them in and out through the entry ports, rotating them in the entry ports, levering (i.e., pivoting) the instruments against external structures of the patient and actuating the end effectors on distal ends of the instruments from outside the patient. The instruments normally pivot around centers defined by the incisions which extend through the skin, muscles, etc. of the patient. The surgeon typically monitors the procedure by means of a television monitor which displays an image of the surgical site captured by the endoscopic camera. Generally, this type of endoscopic technique is employed in, for example, arthroscopy, retroperitoneoscopy, pelviscopy, nephroscopy, cystoscopy, cistemoscopy, sinoscopy, hysteroscopy, urethroscopy, and the like.

While traditional minimally invasive surgical instruments and techniques like those just described have proven highly effective, newer systems may provide even further advantages. For example, minimally invasive robotic (or "telesurgical") surgical systems have been developed to increase surgical dexterity and allow a surgeon to operate on a patient in an intuitive manner. Telesurgery is a general term for surgical operations using systems where the surgeon uses some form of remote control, such as a servomechanism or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient while viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

Typically, a telesurgery system can be provided with at least two master control devices (one for each of the surgeon's hands), which are normally operatively associated with two robotic arms on each of which a surgical instrument is mounted. Operative communication between master control devices and associated robotic arm and instrument assemblies is typically achieved through a control system. The control system typically includes at least one processor which relays input commands from the master control devices to the associated robotic arm and instrument assemblies and from the arm and instrument assemblies to the associated master control devices in the case of, e.g., force feedback, or the like. One example of a robotic surgical system is the DAVINCI™ system available from Intuitive Surgical, Inc. of Mountain View, Calif.

Improvements are still being made in laparoscopic, telesurgery, and other minimally invasive surgical systems and techniques. For example, choosing advantageous locations on a patient for placement of the entry ports continues to be a concern. Many factors may contribute to a determination of advantageous or optimal entry port locations. Factors such as patient anatomy, surgeon preferences, robot configurations, the surgical procedure to be performed and/or the like may all contribute to a determination of ideal entry ports for an endoscope and surgical tools. For example, ports should generally be placed in locations that allow a surgical instrument to reach the target treatment site from the entry port. They should also be placed to avoid collision of two or more robotic arms during a robotic procedure, or that allow free movement of human arms during a laparoscopic procedure. Other factors such as angles of approach to the treatment site, surgeon preferences for accessing the treatment site, and the like may also be considered when determining entry port placement.

If a robotic system is being used, robot positioning must also be determined, usually based at least in part on the port placement. Robotic placement will also typically depend on multiple factors, such as robotic-arm collision avoidance, angles of entry for surgical tools, patient anatomy, and/or the like.

Currently available systems generally do not provide methods or apparatus for determining advantageous entry port placements for laparoscopic, robotic, or other minimally invasive surgery. Although some systems may designate locations for entry ports, they typically do not base those locations on a set of factors such as those just mentioned. Furthermore, currently available systems also do not provide methods or apparatus for validating whether given entry ports will be feasible or for simulating a surgical procedure using the chosen entry ports.

Therefore, it would be advantageous to have methods and apparatus for planning advantageous port placement for laparoscopic, robotic, and other minimally invasive surgery. Such methods and apparatus would ideally also enhance planning of robot placement in robotic surgery. It would also be beneficial to have methods and apparatus which allow verification that a given set of entry ports will be feasible for a given surgical procedure. Ideally, such methods and apparatus would also allow surgeons to simulate a surgical procedure using a set of entry ports and to reject the entry ports if they proved unfeasible. Also ideally, the methods and apparatus would be adaptable for non-surgical uses, such as choosing port placement for robotic entry into non-human systems for various purposes, such as for bomb defusion or handling of hazardous materials.

BRIEF SUMMARY OF THE INVENTION

The present invention generally provides methods, apparatus and systems for enhancing surgical planning. More specifically, the invention provides methods, apparatus and systems which enhance the planning of entry port locations, for entry of surgical tools into a defined volume, such as a body of a patient. The invention also generally provides for enhanced robot positioning in robotic surgery. Such planning is generally accomplished though a method of processing image data of a patient, selecting advantageous port placement based on the processed data, selecting a robot position based on the port placement, and validating port placement and/or simulating an operation using the selected port and robot placements. Thus, embodiments of the present invention provide for more accurate, repeatable robotic operations which require less manual planning from one operation to the next.

In one aspect, a method for identifying advantageous locations for placement of two or more entry ports for performing an operation within a defined volume having a closed surface includes: preparing a model of the defined volume from a set of acquired data; defining at least one target area within the defined volume; and determining from the model and the target area the advantageous locations for placement of the two or more entry ports for performing the operation, the advantageous locations being disposed on the closed surface of the defined volume. Optionally, the determining step may additionally include defining a list of possible locations for placement of each entry port and selecting an advantageous location for placement of each entry port from the list of possible locations for each entry port. In such embodiments, selecting the advantageous locations may be based at least in part on a set of criteria, the criteria including at least one of robot kinematics, robot kinetics, robot work range, deviation of tool entry angle from normal, organ geometry, surgeon defined constraints, robot force limitations, and patient force limitations. In other embodiments, selecting the advantageous location for placement of each entry port is based at least in part on a cost function, the cost function at least partially defined by at least one of minimizing deviations from a desired configuration, arm placement symmetry with respect to endoscope positioning, and minimization of tool entry angle with respect to surface normal.

In some embodiments, the operation comprises a surgical operation on a body of a patient and the defined volume comprises a volume of at least a portion of the body. In other embodiments, the operation comprises an operation on a munitions material, the operation including at least one of inspection, maintenance, disabling, and mechanical interaction. Typically, the acquired data comprises imaging data acquired using at least one of computed tomography and magnetic resonance imaging, though other modalities may be used.

As mentioned briefly above, some embodiments include determining a position for placement of a robot relative to the defined volume for performing the operation. In such embodiments, determining the position of the robot may be based at least in part on a set of criteria, the criteria including at least one of robot kinematics, robot kinetics, robot work range, deviation of tool entry angle from normal, organ geometry, surgeon defined constraints, robot force limitations, and patient force limitations.

As also mentioned above, some embodiments include providing a first simulation for enabling a user to simulate the operation, the first simulation based upon the model of the defined volume, the target area, and the advantageous locations of the entry ports. Where a simulation is provided, some embodiments will also enable the user to reject one or more of the advantageous locations based on the first simulation, determine different advantageous locations based on the user's rejection, and provide a second simulation for enabling the user to simulate the operation, the second simulation being based upon the model of the defined volume, the target area, and the different advantageous locations of the entry ports.

In another aspect, a method for identifying advantageous locations for placement of two or more entry ports for performing a surgical operation on a body of a patient includes preparing a model of at least a portion of the patient's body from a set of acquired data, using the model to define at least one target area within the body, defining a list of possible locations for each of the two or more entry ports, the possible locations being disposed on a surface of the body, and selecting an advantageous location for placement of each of the two or more entry ports from each list of possible locations.

In yet another aspect, a method for identifying advantageous locations for placement of two or more entry ports for performing a surgical procedure on a body of a patient includes defining a list of possible locations for each of the two or more entry ports, the possible locations being disposed on a surface of the body, selecting, based on a set of criteria, an advantageous location for placement of each of the two or more entry ports from each list of possible locations, verifying that the selected location for placement of each entry port is feasible, and providing means for simulating the surgical procedure. In some embodiments, the set of criteria includes at least two of robot kinematics, robot kinetics, robot work range, deviation of tool entry angle from normal, organ geometry, surgeon defined constraints, robot force limitations, and patient force limitations. In other embodiments, the set of criteria includes a cost function, the cost function at least partially defined by at least one of minimizing deviations from a desired configuration, arm placement symmetry with respect to endoscope positioning, and minimization of tool entry angle with respect to surface normal.

In another aspect, an apparatus for identifying advantageous locations for placement of two or more entry ports for performing an operation within a defined volume having a closed surface includes a computer software module for identifying the advantageous locations, and a computerized simulation device for simulating the operation using the computer software and the advantageous locations.

In yet another aspect, a system for performing a robotic operation within a defined volume having a closed surface includes a robot having at least two robotic arms, a computer coupled with the robot for at least partially controlling movements of the robotic arms, and computer software couplable with the computer for planning advantageous locations for at least two entry ports into the defined volume by the at least two robotic arms and for providing a simulation of the robotic operation. Optionally, the robot may include at least two robotic arms for attaching surgical tools and at least one robotic arm for attaching an imaging device. Also optionally, the computer may include a display device for displaying the simulation of the robotic operation.

BRIEF DESCRIPTION OF THE DRAWINGS

FIG. 7b is a close-up perspective view of the validation in FIG. 7a.

FIG. 7c is a side view of a computer validation of a surgical procedure as shown in FIG. 7a.

DETAILED DESCRIPTION OF THE INVENTION

The present invention generally provides methods and apparatus for enhancing planning of laparoscopic, robotic, and other minimally invasive surgery. More specifically, various embodiments provide methods and apparatus for planning advantageous locations for placement of two or more entry ports for accessing a defined volume, such as a patient, with surgical tools to perform a minimally invasive operation. In robotic surgery, robot position will typically also be planned. Additionally, many embodiments provide validation that selected entry port placements and/or robot positions will be feasible for a given operation. Many embodiments also provide simulation of a given operation, using selected entry port placements and/or robot positions, to allow a surgeon or other user to practice using the surgical system.

Although the following description focuses on planning port placement and robot position in a robotic surgery context, specifically in a heart surgery context, many other applications are contemplated within the scope of the invention. As mentioned above, for example, various embodiments may be used in other surgical contexts, such as non-robotic laparoscopic/abdominal surgery, arthroscopy, retroperitoneoscopy, pelviscopy, nephroscopy, cystoscopy, cistemoscopy, sinoscopy, hysteroscopy, urethroscopy, and the like. Furthermore, non-surgical applications are contemplated, including but not limited to handling, disabling, maintaining and/or the like of munitions, hazardous materials, and/or other suitable materials. Within the surgical context, methods and apparatus of the present invention may be used with many different systems for conducting robotic or minimally invasive surgery. One example of a robotic surgical system which may incorporate methods and apparatus of the present invention is the DAVINCI™ system available from Intuitive Surgical, Inc. of Mountain View, Calif. Many other surgical systems and apparatus may be used, however. Therefore, the following description is provided for exemplary purposes only and should not limit the scope of the present invention as set forth in the appended claims.

Figure 1:
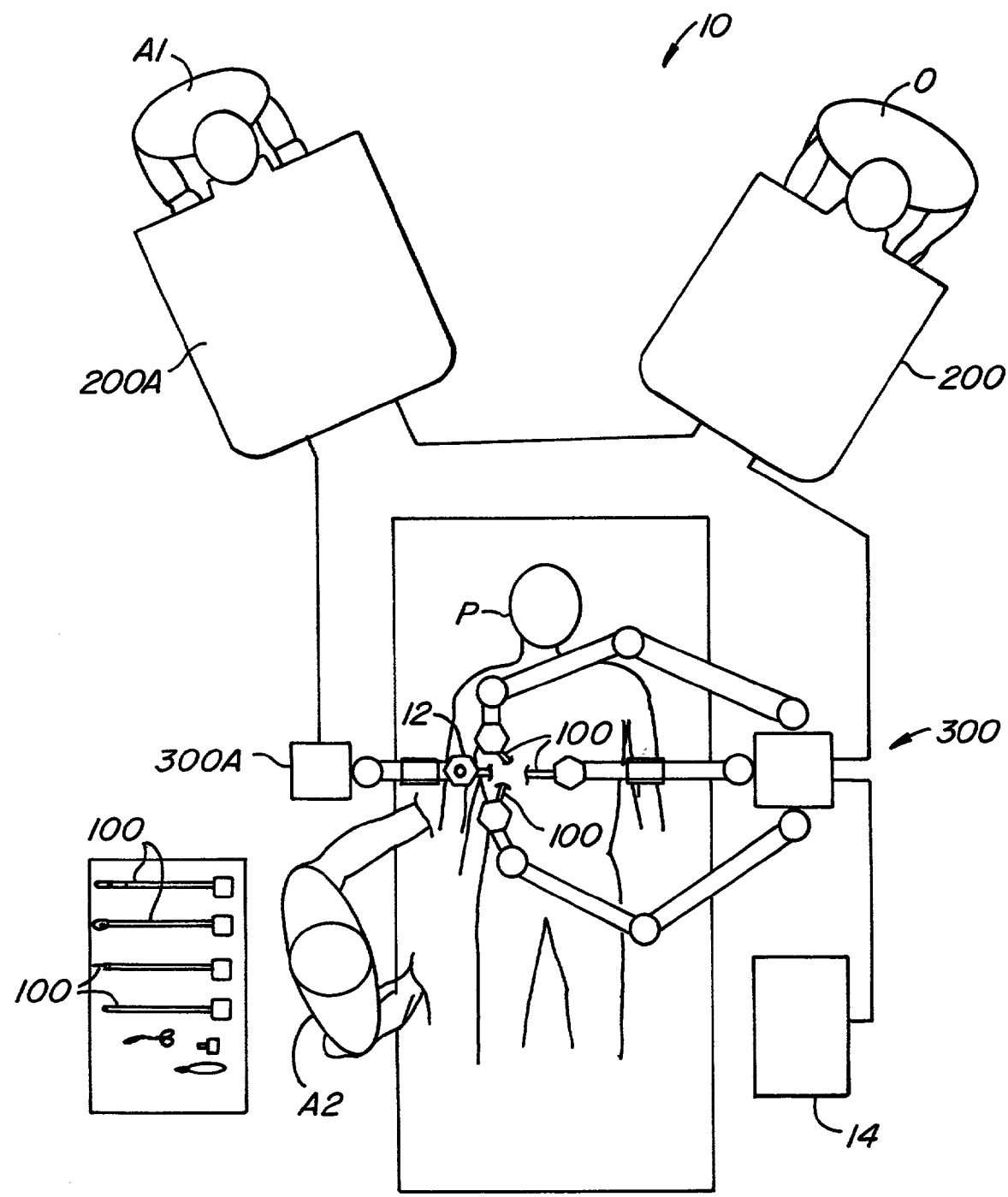
FIG. 1 is an overhead view of a robotic surgical system for use in an embodiment of the present invention.

Referring now to FIG. 1, one example of a robotic surgical system 10, with which the methods and apparatus of the present invention may be used, includes a master control station 200 and a slave cart 300. Optionally, any of several other additional components may be included in the surgical system to enhance the capabilities of the robotic devices to perform complex surgical procedures. An operator O performs a minimally invasive surgical procedure at an internal surgical site within patient P using minimally invasive surgical instruments 100. Operator O works at master control station 200. Operator O views a display provided by the workstation and manipulates left and right input devices. The telesurgical system moves surgical instruments mounted on robotic arms of slave cart 300 in response to movement of the input devices. As described in co-pending U.S. patent application Ser. No. 09/436,527, filed on Dec. 14, 2001, the full disclosure of which is incorporated herein by reference, a selectively designated "left" instrument is associated with the left input device in the left hand of operator O and a selectively designated "right" instrument is associated with the right input device in the right hand of the operator.

As described in more detail in co-pending U.S. patent application Ser. No. 09/373,678 entitled "*Camera Reference Control in a Minimally Invasive Surgical Apparatus*," filed Aug. 13, 1999 (the full disclosure of which is incorporated herein by reference) a processor of master controller 200 will preferably coordinate movement of the input devices with the movement of their associated instruments, so that the images of the surgical tools, as displayed to the operator O, appear substantially connected to the input devices in the hand of the operator.

Optionally, an auxiliary cart A can support one or more additional surgical tools 100 for use during the procedure.

One tool is shown here for the illustrative purposes only. A first assistant A1 is seated at an assistant control station 200A, the first assistant typically directing movement of one or more surgical instruments not actively being manipulated by operator O via master control station 200, such as a tissue stabilizer. A second assistant A2 may be disposed adjacent patient P to assist in swapping instruments 100 during the surgical procedure. Auxiliary cart A may also include one or more assistant input devices 12 (shown here as a simple joystick) to allow second assistant A2 to selectively manipulate one or more surgical instruments while viewing the internal surgical site via an assistant display 14. Preferably, the first assistant A1 seated at console 200A has the same image as the surgeon seated at console 200.

Master control station 200, assistant controller 200A, cart 300, auxiliary cart 300A, and assistant display 14 (or subsets of these components) may allow complex surgeries to be performed by selectively handing off control of one or more robotic arms between operator O and one or more assistants. Alternatively, operator O may actively control two surgical tools while a third remains at a fixed position. For example, to stabilize and/or retract tissues, with the operator selectively operating the retracting or stabilizer only at designated times. In still further alternatives, a surgeon and an assistant can cooperate to conduct an operation without either passing control of instruments or being able to pass control of instruments with both instead manipulating his or her own instruments during the surgery.

Although FIG. 1 depicts two surgeon consoles controlling the two cart structures, a preferred embodiment comprises only one console controlling four or more arms on two carts. The scope may optionally be mounted on the auxiliary cart, and three tissue manipulator arms may be mounted on the main cart. In some embodiments, one or more tools, particularly tissue stabilizers, may not be actively driven, instead being positioned by manually actuating a drive system of the tool and then locking the tool into position.

Figure 2:
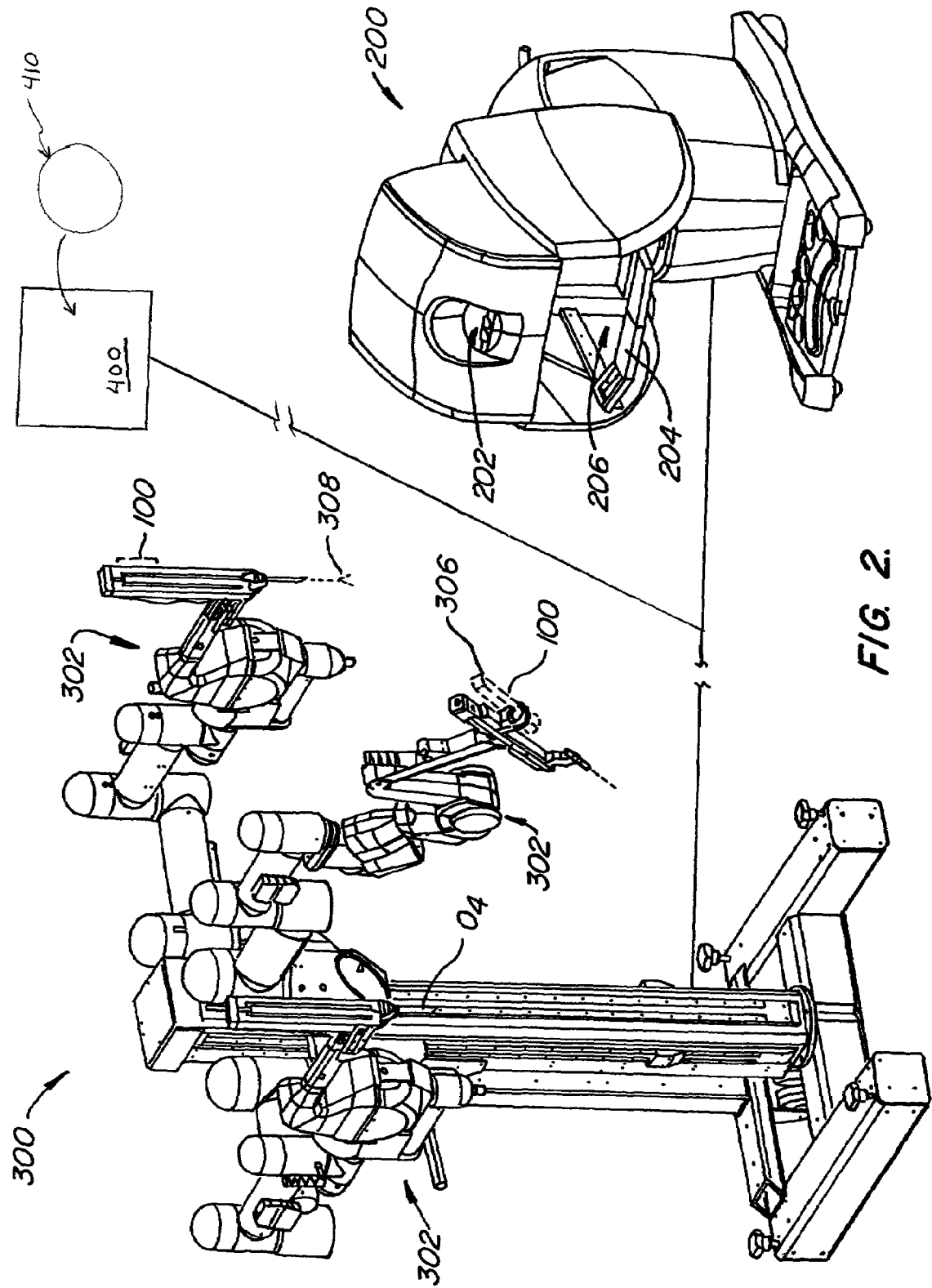
FIG. 2 is a perspective view of a master control workstation and a patient-side cart having three robotic manipulator arms for use in the system of FIG. 1.

Referring now to FIG. 2, master control station 200 includes a viewer 202 wherein an image of a surgical site is displayed in use. A support 204 is provided on which the operator, typically a surgeon, can rest his or her forearms while gripping two master controls, one in each hand. Master controls are positioned in a workspace 206 disposed inwardly beyond support 204. When using workstation 100, the surgeon typically sits in a chair in front of the workstation, positions his or her eyes in front of the viewer 202 and grips the master controls.

FIG. 2 shows also the surgical manipulator slave or cart 300 of the telesurgical system. In use, cart 300 is positioned close to a patient for surgery, and the base of the cart is caused to remain stationary until the surgical procedure has been completed. Cart 300 here includes three robotic manipulator arm assemblies 302, each manipulator supporting an instrument 100. More specifically, one of the robotic arm assemblies supports an image capture device, such as an endoscope 306 (which is coupled to display 102 of the workstation). Each of the other two manipulator arms supports a tissue manipulation tool 308 having a surgical end effector for treating tissue.

Finally, FIG. 2 shows a processor 400 coupled with master control station 200 and cart 300 and a tangible medium 410 embodying machine readable code, or software. The software typically includes instructions which enable various embodiments of the methods of the present invention. The tangible medium 410 may be coupled with the processor 400 for use. Generally, the software may be used with any suitable hardware, such as a personal computer work station with graphics capabilities, such as but not limited to a PENTIUM III® or equivalent processor with a GEFORCE2® graphics card. Other hardware which may be used with software of the present invention includes a display monitor, such as a 17" monitor, a processor with 256 Mbytes of RAM and a 10 Gigabytes hard disk. Input devices will typically include a mouse and may also include a 3D mouse or a PHANTOM® arm.

Although in some embodiments, as just described, hardware will include a stand-alone PC workstation or similar stand-along hardware, other embodiments will be integrated with an existing system. For example, hardware may be embedded in a dedicated apparatus such as a robotic surgical system. In one embodiment, hardware is embedded in a part of DAVINCI® robotic system (Intuitive Surgical, Inc., Sunnyvale, Calif.) such as the master control station 200.

The robotic manipulator arms will move and articulate the surgical tools in response to motions of the input devices at the workstation, so that the surgeon can direct surgical procedures at internal surgical sites through minimally invasive surgical apertures. The workstation 200 is typically used within an operating room with the cart, but can be positioned remote from the cart, even miles away. An exemplary master control input device for manipulation by the surgeon is more fully described in co-pending U.S. patent application Ser. No. 09/398,507, entitled "*Master Having Redundant Degrees of Freedom*," as filed on Sep. 17, 1999, the full disclosure of which is incorporated herein by reference. Exemplary manipulator arms are more fully described in co-pending U.S. patent application Ser. No. 09/368,309 as filed on Aug. 3, 1999, for a "*Manipulator Positioning Linkage for Robotic Surgery*," (the full disclosure of which is also incorporated herein by reference), which also describes manually positionable linkages supporting the manipulators. It should be noted that a number of alternative robotic manipulator arms might be used, including those described in U.S. Pat. No. 5,855,583, the full disclosure of which is also incorporated herein by reference.

Figure 3:
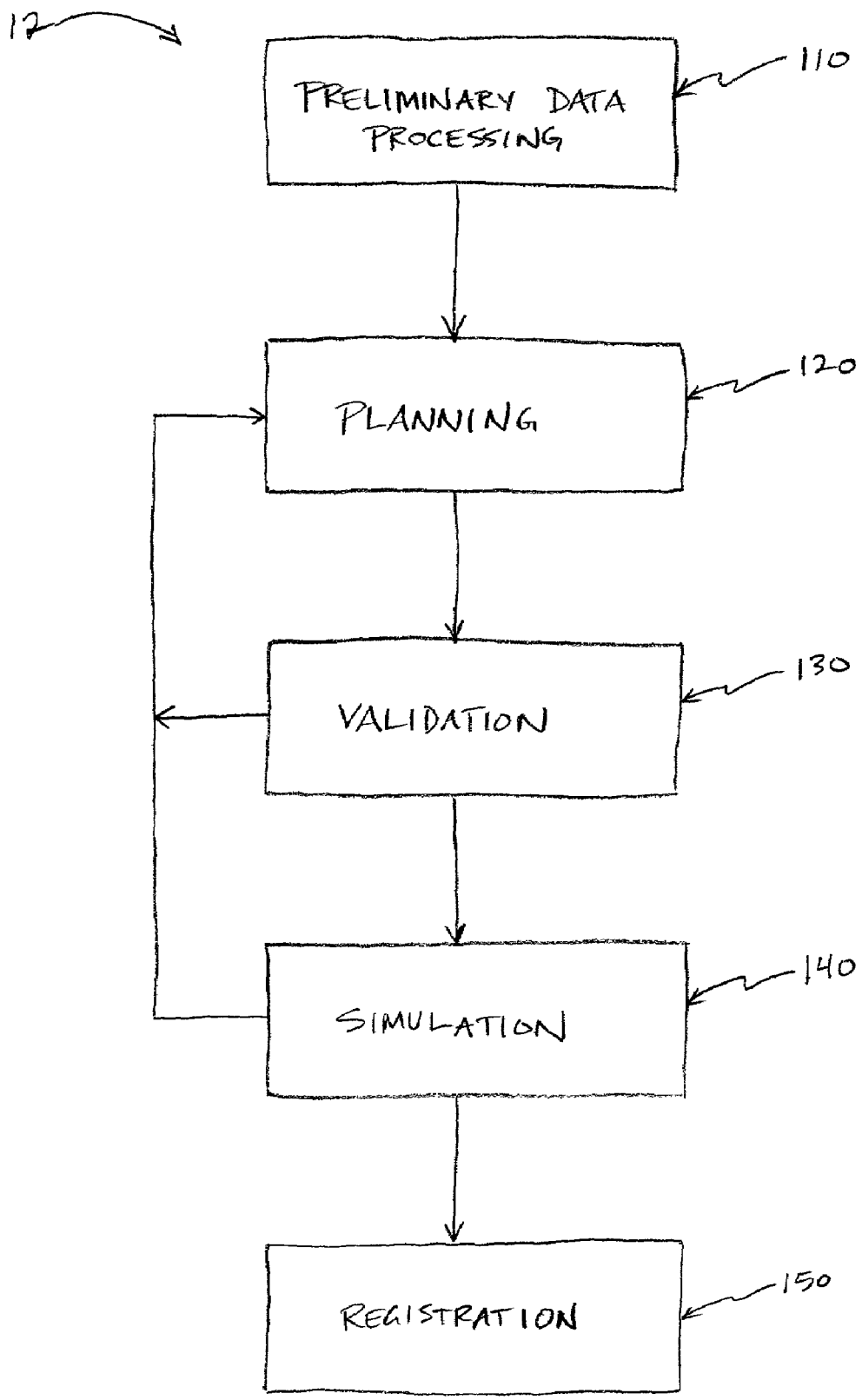
FIG. 3 is a flow diagram of a method for enhancing port placement in robotic operations according to an embodiment of the present invention.

Referring now to FIG. 3, a method for enhancing port placement 12 suitably includes four general steps or stages. In various alternative embodiments, certain steps may be combined, other steps may be added, and/or one or more steps may be eliminated, without significantly changing the overall result. That being said, four general stages used to plan entry port placement may include preliminary data processing 110, planning 120, validation 130 and simulation 140.

Preliminary data processing 110 generally includes processing imaging data, such as radiological data from computed tomography (CT) and/or magnetic resonance imaging (MRI) scans. Such processing may include segmentation, 3D reconstruction, robot modeling and/or the like. Planning 120 generally includes choosing locations for two or more entry ports into a defined volumetric space, such as a patient, for allowing entry of surgical tools, robotic tools or arms, one or more endoscopes, retractors, and/or the like. Typically, planning 120 involves combining data in an optimization algorithm where mathematical criteria have been integrated. The criteria translate features such as collision avoidance between the manipulator arms and reachability of targeted organs. Validation 130 refers to a process of testing the feasibility of the operation by reproducing the expected movements of the surgeon and looking for collisions or other problems, such as an out of reach condition. Finally, simulation 140 allows a surgeon or other user to use the chosen entry ports and robot position to perform a practice operation. In many embodiments, if the surgeon judges the proposed ports and/or robot position less than optimal, the surgeon may reject the chosen locations and new ones may be chosen by the system.

Figure 4:
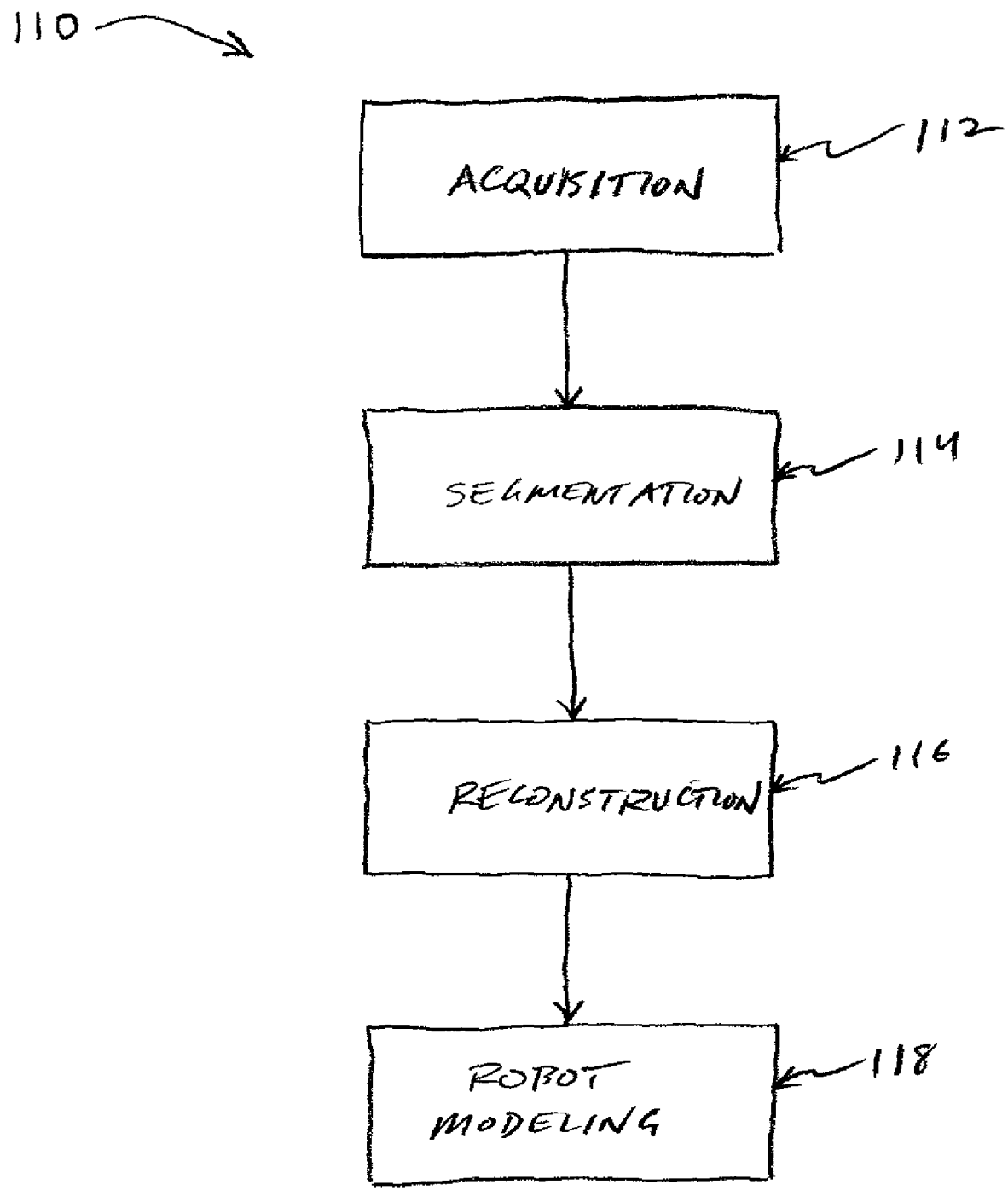
FIG. 4 is a flow diagram of the preliminary data processing stage of a method as in FIG. 3 according to an embodiment of the present invention.

Each of the steps or processes described above may involve various components or steps in various embodiments. For a more detailed discussion of each step, see the master's thesis of Louai Adhami, attached as Exhibit C to U.S. Provisional Patent Application Ser. No. 60/296808, previously incorporated by reference. For example, with reference to FIG. 4, some embodiments include multiple stages or steps at the preliminary data acquisition 110 phase. In one embodiment, for example, steps include data acquisition 112, segmentation 114, reconstruction 116 and robot modeling 118. Again, in various embodiments these steps may be carried out in any suitable order and/or steps may be added, eliminated, and/or carried out simultaneously.

Data acquisition 112 generally involves acquiring any data regarding a volume which is to be operated upon, such as a portion of a patient's body, as well as, in some embodiments, data regarding a robot, surgical tools, and the like, to be used in performing the operation. Data may include, for example, CT scan data, with or without contrast, MRI data, coronary artery angiograms, conventional radiographs, digital representations of conventional radiographs, and/or the like. In a totally endoscopic coronary artery bypass graft (TECAB) operation, for example, CT scan data is typically used. This generally involves acquiring helical CT scans of a patient, with 3 mm spacing, from approximately the neck region to the hip region of the patient. Slice size is often decreased to 1 cm in the area of the heart, to acquire more image information, and often a dye is injected to better visualize the heart and aorta. Additionally, such CT data acquisition will often be synchronized with electrocardiogram (ECG) data acquisition. Coronary angiograms may also be acquired, to enable an accurate diagnosis of the state of heart vessels. Data from multiple types of imaging studies, such as CT scans and angiograms, may be used together in various embodiments to enhance planning of port placement.

Segmentation 114 generally first involves separating out different anatomical entities within the defined volume of the operation, such as various anatomical organs and tissues within a patient. For a TECAB procedure, for example, bones (such as ribs), heart, and left inferior mammary artery (LIMA) are typically segmented. Segmentation of bones from surrounding soft tissues is automatically performed, based on the significantly higher density of the bones, by the "extractcontour" computer software. ("Extractcontour" is software developed by INRIA Sophia Antipolis, and is in the public domain and available from INRIA.) Heart and LIMA segmentation are generally performed manually, such as by a radiologist or other suitable technician. The LIMA is approximated by a fixed-size circle on each CT slice, in an area specified manually. The heart is approximated by splines built around a set of points that are manually drawn. Typically, this process is invariant from one patient to another, meaning that it does not require adjustments by a radiologist or other radiology technician between patients.

Another part of the segmentation step 114 is to define admissible points for entry into the defined volume, as well as admissible directions for entry. In other words a list is compiled of possible entry points and directions. Admissible points of entry are sites on a surface of the volume that allow the introduction of robot arms, an endoscope, and/or any other tools to be used for the operation. In a TECAB operation, for example, admissible points may include any points within the intercostal spaces (spaces between the ribs) of a patient. Points which would cause a tool to pass through bone, such as a rib, are typically eliminated as not being admissible. Admissible directions are directions generally pointing outward and perpendicular to the skin, which replicate directions of orientation that robotic arms, endoscopes and the like will have during the operation.

Another component in preliminary data processing 110 is reconstruction 116. Reconstruction 116 generally refers to formation of acquired, segmented data into a 3-dimensional model of the defined volume which will be operated upon. Generally, such 3D models are constructed using computer software, such as the nuages software, described in Bernhard. Geiger, "Three Dimentional Modeling of Human Organs and its Application to Diagnosis and Surgical Planning," Technical Report 2105, INRIA-Sophia, 1993, the entire contents of which is hereby incorporated by reference. A public version of nuages software is available at ftp://Hftp-sop.inria.fr/prisme/NUAGES/Nuages. Again, this software may be run on conventional, off-the-shelf hardware, such as a PENTIUM III® processor. The underlying algorithm used for reconstruction 116 via nuages software is based on projected Voronoï diagrams, where the input is a set of closed non-intersecting contours, and the output is a mesh of triangles representing the reconstructed surface in 3D. This algorithm has the advantages of outputting a relatively low, manageable number of triangles and of not being prone to distortive effects such as the staircase effect observed in marching cubes algorithms.

Another aspect of preliminary data processing 110, in some embodiments, includes robot modeling 118. Generally, robot modeling 118 involves combining a geometric model of a robot with the acquired radiological data from the patient or other defined volume in an interactive interface. In the preliminary phase, for example, Denavit-Hartenberg (DH) models may be used, along with a generic C++ library, where OPENGL™ output and collision detection are implemented. In one embodiment two primitives are retained for the modeling of the robot body, namely rectangular parallelepipeds and cylinders. Part of robot modeling 118 typically includes using inverse kinematics, either analytically or numerically, to detect possible interferences between links of the robot. In other words, collision detection is carried out. For efficiency purposes, a dedicated interference detection method may include a hierarchical method based on direct collision tests between the different modeling primitives (cylinders and rectangular parallelepipeds), in addition to spheres. This method can be extended accordingly if the model is refined with more complex primitives.. An analytic solution is used when there is the same number of degrees of freedom (dofs) and constraints, whereas a numerical solution is used when there are more dofs than constraints. In the latter case, artificial constraints are added to reflect the proximity between the arms, which would be of great significance when dealing with the problem of collision avoidance.

With reference again to FIG. 3, after preliminary data processing 110 planning 120 is performed. Planning 120 generally consists of identifying advantageous locations for two or more entry ports for accessing the defined volume to be operated upon. In many embodiments, planning 120 also includes planning one or more positions of a robot and/or its component parts for performing an operation, with the robot positioning being based on the advantageous locations of the two or more entry ports. Typically, planning 120 is carried out to identify optimal or advantageous entry port locations for three tools, such as two robot arms and an endoscope. Multiple criteria are generally used to help identify such locations, and the locations are selected from among the admissible entry points described above. Thus, one embodiment involves choosing a "triplet" of three entry points that optimizes a set of predefined criteria. The criteria may be any suitable criteria, such as robot constraints, anatomical constraints, surgeon preferences, and/or the like.

In one embodiment, for example, some criteria are derived from surgeon preferences. For example, a surgeon may specify target points within the patient or other defined volume on which the surgeon wants to operate, such as points on or in a heart in heart surgery. Target points may then be used to define a target area, within which the surgeon wishes to operate. The surgeon also typically defines one or more preferred "attack directions," which are generally directions from which the surgeon prefers to access the target points. "Attack angles" may be derived from these attack directions. An attack angle is an angle between the attack direction at the target point on the one hand, and the straight line connecting the latter to an admissible point (on a surface of the patient) on the other. It reflects the ease with which the surgeon can operate on a given location with respect to the attack direction chosen by the surgeon. A "dexterity parameter" is another criteria which may be used. The dexterity parameter is proportional to the angle between the surface normal at the admissible point and a straight line connecting the latter to the target point. This measure of dexterity is typically interpreted in accordance with the robot capabilities.

Figure 5:
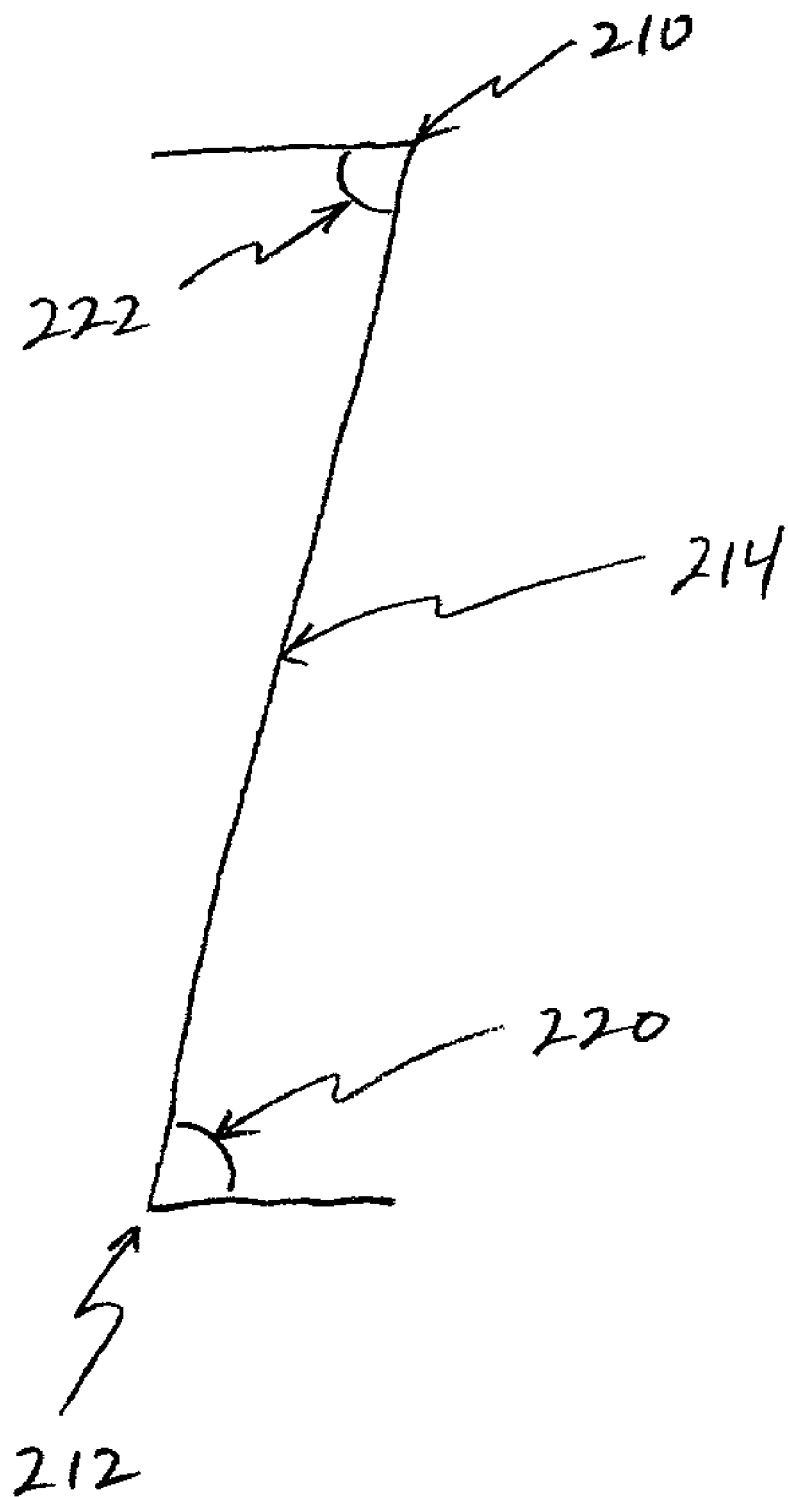
FIG. 5 is a line diagram showing various angles between an entry port location and a target area according to an embodiment of the present invention.

Other criteria which may be used in identifying advantageous locations for entry ports include both qualitative and quantitative criteria. Referring now to FIG. 5, qualitative criteria, for example, may relate to the reachability from an admissible point 210 to a target point 212, with the admissible point being eliminated from consideration if a tool to be used in the operation is not long enough to reach across distance 214 to reach target point 212.

In another criteria, an admissible point may be eliminated if an angle 222 between a surface of the patient at the entry point and a line from the entry point to the target point 212 is too large, such that use of a tool through that entry point may cause damage to a nearby structure. Use of such an entry point in a heart operation, for example, may cause damage to a rib. Yet another criteria which might be used to eliminate an admissible point would be if the combination of the admissible entry point, surgical tool, attack direction and target point would result in the tool passing through an anatomic structure. For example, if the tool would pass through a lung on its way to the heart, that admissible point would be eliminated. Computer graphics hardware may be used to perform this test in a method similar to that described in "Real-time Collision Detection for Virtual Surgery," by J.-C. Lombardo, M. P. Cani and F. Neyret, *Computer Animation, Geneva,* May 1999, the entire contents of which is hereby incorporated by reference.

Quantitative criteria generally relate to dexterity of the robot, where each admissible point is graded based on an angle 212 between the attack direction and the line relating target point 212 to admissible point 210. This measure translates the ease with which the surgeon will be able to operate on target areas from a given port in the case of a robotic tool, or the quality of viewing those areas via an endoscope.

Criteria such as those described above may be applied in various orders and by various means. In one embodiment, for example, identifying an advantageous triplet of entry port locations is accomplished in two basic steps: First an entry port for an endoscope is chosen based on various criteria, then admissible entry port locations for two (or another number) tools are ranked according to their combined quantitative grade and their position with respect to the endoscope. More precisely, the triplet (of endoscope port and two tool ports) is ranked to provide a desirable symmetry between two robot arms and the endoscope, and to favor positions of the robot arms at maximum distances from the endoscope to provide the surgeon with a clear field of view.

Applying criteria in this way may involve several steps. For example, in one embodiment a first step involves eliminating admissible entry port location candidates that will not provide access to the target areas. In a next step, admissible sites for an endoscope are sorted to minimize the angle between the target normal and the line connecting the admissible point to the target point. This step gives precedence to entry ports for the endoscope that provide a direct view over the target areas and, therefore, ports which would create angles greater than a desired camera angle are eliminated. In applying such criteria, targets areas may be weighted according to their relative sizes. For robot arms, admissible entry points may be sorted in the same way as for the endoscope, but with the angle limitation relaxed. Admissible candidates that make too obtuse an angle between the tool and the skin may be eliminated. For example, an maximum angle of 60° may be chosen in a heart operation to avoid excessive stress on the ribs. Finally, a triplet combination of three entry ports (or however many entry ports are to by used) may be chosen to optimize the criteria discussed above while also maximizing the distances between the ports. This distance maximization criteria will prevent collision between robot arms and allow the surgeon to operate the robotic arms with a relatively wide range of movement.

Once a set of advantageous entry port locations has been selected, an advantageous position for placement of the robot to be used, in relation to the patient, is typically determined. Robot positioning will typically be based on the entry port placement and the robot configuration, such that the robot is positioned in a way that avoids collisions between robot arms and allows the arms to function in performing a given operation without violating any of a number of selected constraints. Constraints may include, for example, number of robot arms and number of degrees of freedom for each arm, potential collisions between the robot arms, potential collisions between an arm and the patient, other potential collisions (e.g. with anesthesia equipment or operating room table), and/or miscellaneous constraints (e.g. endoscope orientation for assistant surgeon). Certain constraints may be more subjective, such as surgeon preferences, operating room configurations and the like.

To determine an advantageous robot position, one method uses a combined probabilistic and gradient descent approach, where configurations of the passive joints (including a translation of the base) are randomly drawn in robot articular space. To each configuration, a cost function is associated that depends on the constraints discussed above. A low cost function gives its corresponding robot configuration a high selection probability. This process is repeated until a configuration arrives at a cost function that is less than a given threshold. Once the cost function is low enough (i.e., the passive joints are close enough to the desired port), the active joints are moved over all the targets (using inverse kinematics), to verify that there are no collisions.

Returning to FIG. 3, once a suitable triplet or other configuration of entry port locations has been identified, validation 130 is performed to verify that the identified locations are feasible for carrying out the given operation. In most embodiments, the robot is placed in the position which has been selected and movement of the robot as will be done during the operation is carried out to look for possible collisions between the robot arms. Generally, the trajectory between two target areas is a straight line, and this is the way a surgeon is expected to navigate. The possibility of collisions between discrete time steps is handled by an interference detection algorithm that tests sweeps the volume covered by the manipulator arms. In addition to interference detection, out of reach conditions and possible singularities are monitored and signaled. Finally, the endoscope is positioned relative to the tips of the tool arms at a predefined distance, in a way to guarantee a good visibility at all times. If no problem is detected during validation 130, then the triplet or other configuration is accepted and a surgeon may proceed with simulation 140. If there is a collision or other problem, the system may return to the planning stage 120 to select other entry port locations.

Simulation 140 generally provides a surgeon or other operator of a robotic system an environment in which to practice a given operation to develop facility with the robot and to re-validate the selected, advantageous entry port locations. Generally, simulation 140 is carried out using robotic control mechanisms, a computer with a monitor, and computer software to enable the simulation. Thus, the validation 130 step just described and the simulation step 140 are typically carried out using computerized systems. Using simulation 140, a surgeon can essentially perform the operation as it would be performed on a live patient, as simulated on a 3-dimensional representation on a computer monitor, to practice use of the robotic system and to confirm that the selected combination of robot position and entry port locations is feasible.

Figure 6:
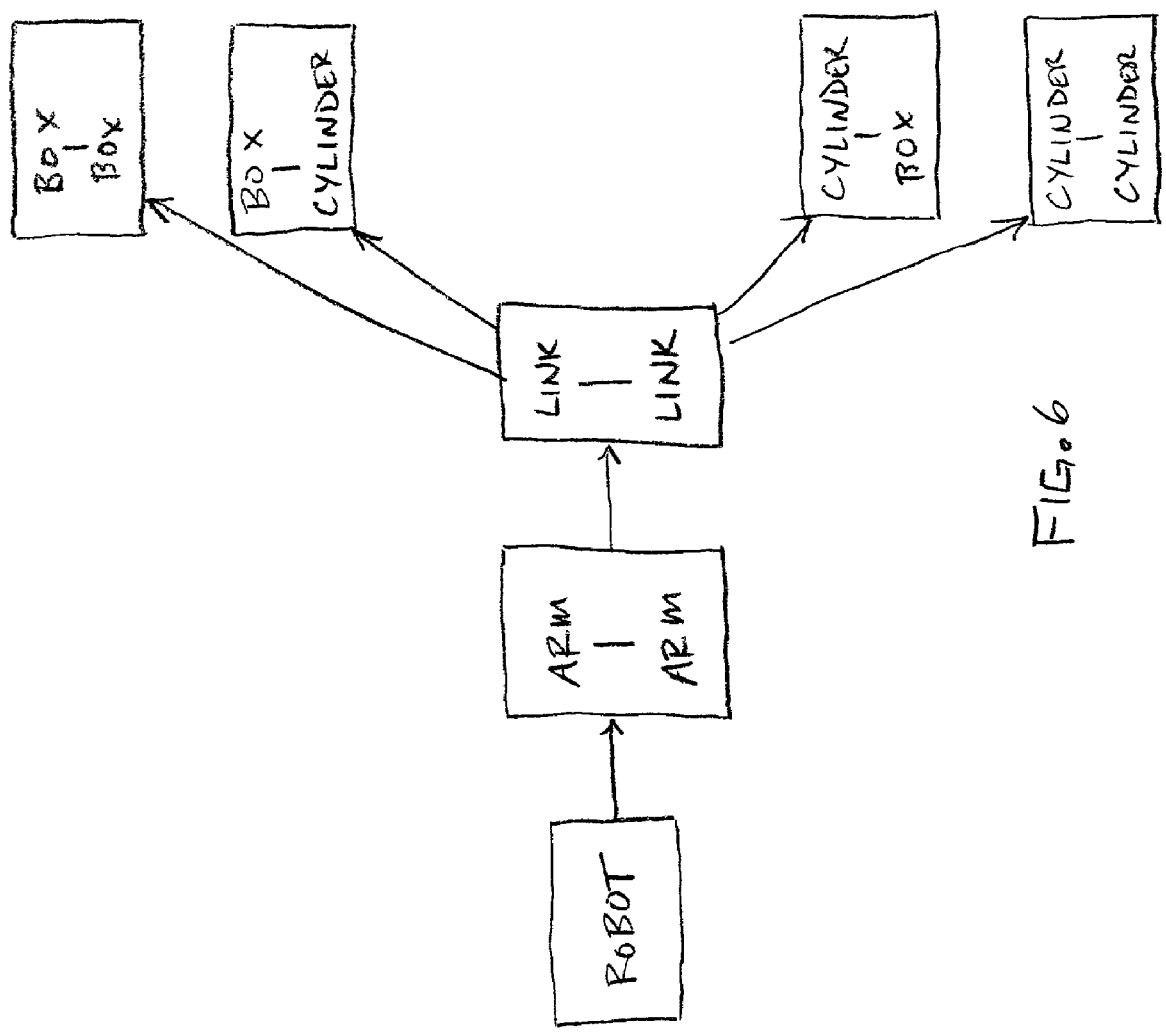
FIG. 6 is a diagram of an internal collision detection logic used in an embodiment of the present invention.

As with the validation step 130, simulation 140 typically includes collision detection for possible collisions between the robot arms. Collisions are typically stratified as internal (between the manipulators) and external (with the anatomical entities). Internal collisions may be further divided into static and dynamic (continuous movement) collisions. In most embodiments, an algorithm is used to detect possible internal collisions, the algorithm detecting interferences between rectangular parallelepipeds and cylinders. FIG. 6, for example, shows a diagram of an internal collision detection logic which may be used. In that logic, testing for an intersection between two boxes is accomplished by looking for an overlap between one of the boxes and the sides of the other. The same can be done for two cylinders or between a box and a cylinder. For further details regarding this algorithm, see master's thesis of Louai Adhami, attached as Exhibit C to U.S. Provisional Patent Application Ser. No. 60/296808, which has previously been incorporated by reference. (Also see doctoral thesis of Louai Adhami, available from INRIA Sophia after Jul. 3, 2002.)

External collisions, on the other hand, are typically detected using graphics hardware and a method such as that suggested in "Real-time Collision Detection for Virtual Surgery," by J.-C. Lombardo, M. P. Cani and F. Neyret, *Computer Animation, Geneva,* May 1999, previously incorporated herein by reference. Sufficient graphics hardware may include, for example, a personal computer work station with graphics capabilities, such as a PENTIUM III® or equivalent processor with a GEFORCE2® graphics card, and any suitable monitor.

Figure 7A:
FIG. 7a is a side view of an experimental validation of the results of a surgical procedure using methods and apparatus of an embodiment of the present invention.
Figure 7B:
Figure 7D:
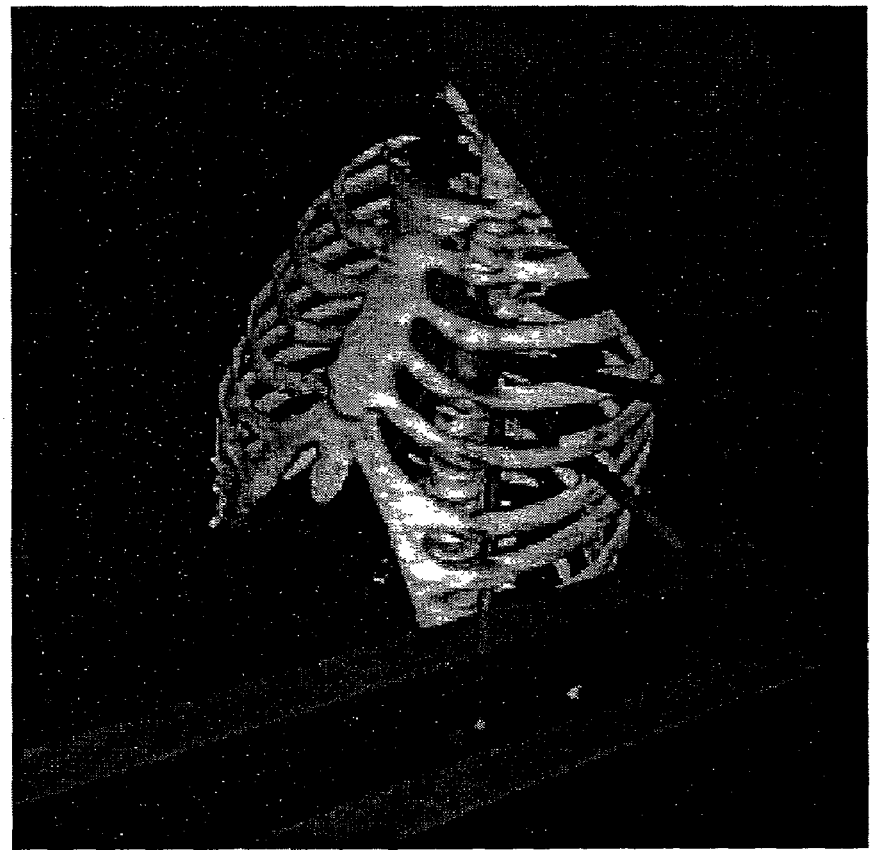
FIG. 7d is a perspective view of a computer validation of a surgical procedure as shown in FIG. 7b.
Figure 7E:
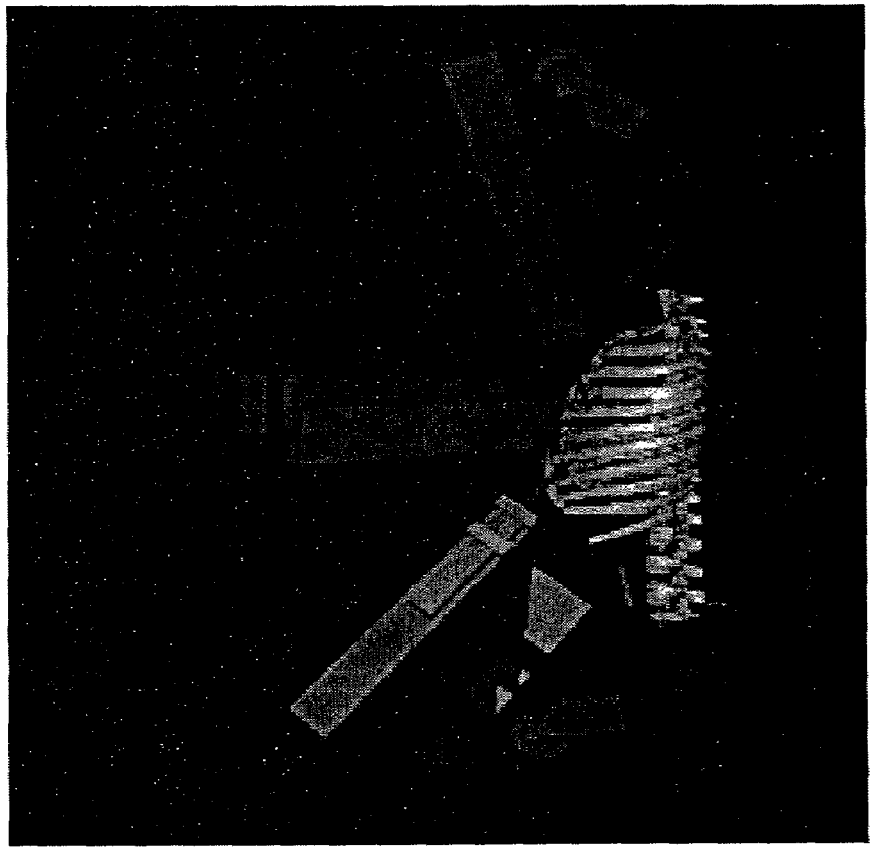

Referring now to FIGS. 7a-d, a system for planning, validating, and simulating port placement may first be calibrated, or experimentally adjusted, using a physical, structural modeling system. For example, FIGS. 7a and 7b show an experimental validation of port placement and robot position for a TECAB procedure using a skeleton rib cage. FIGS. 7c and 7d show a computerized representation of the same exerpeimental validation. Such physical validation on a skeleton, cadaver, or other structural model will not be necessary in typical use of the methods and apparatus of the present invention. Generally, validation 130 and simulation 140 steps will be carried out using the robotic system and a computerized system, and will not involve physical, structural models. If use of such models were found to be advantageous for general use of various embodiments, however, such models are within the scope of the present invention.

Figure 8A:
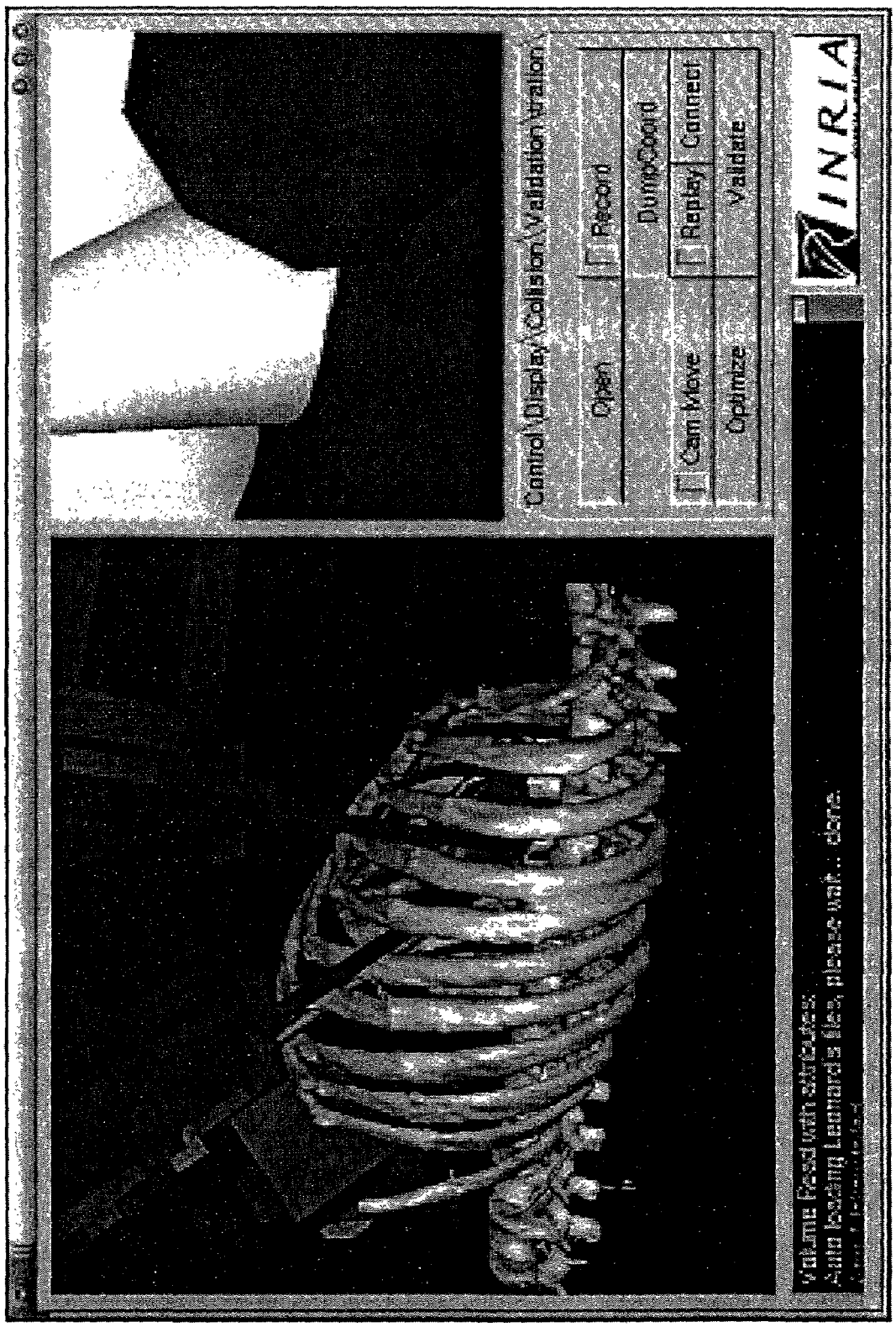
FIG. 8a is a screen shot side view of a computer interface for simulation of a surgical procedure according to an embodiment of the present invention.
Figure 8B:
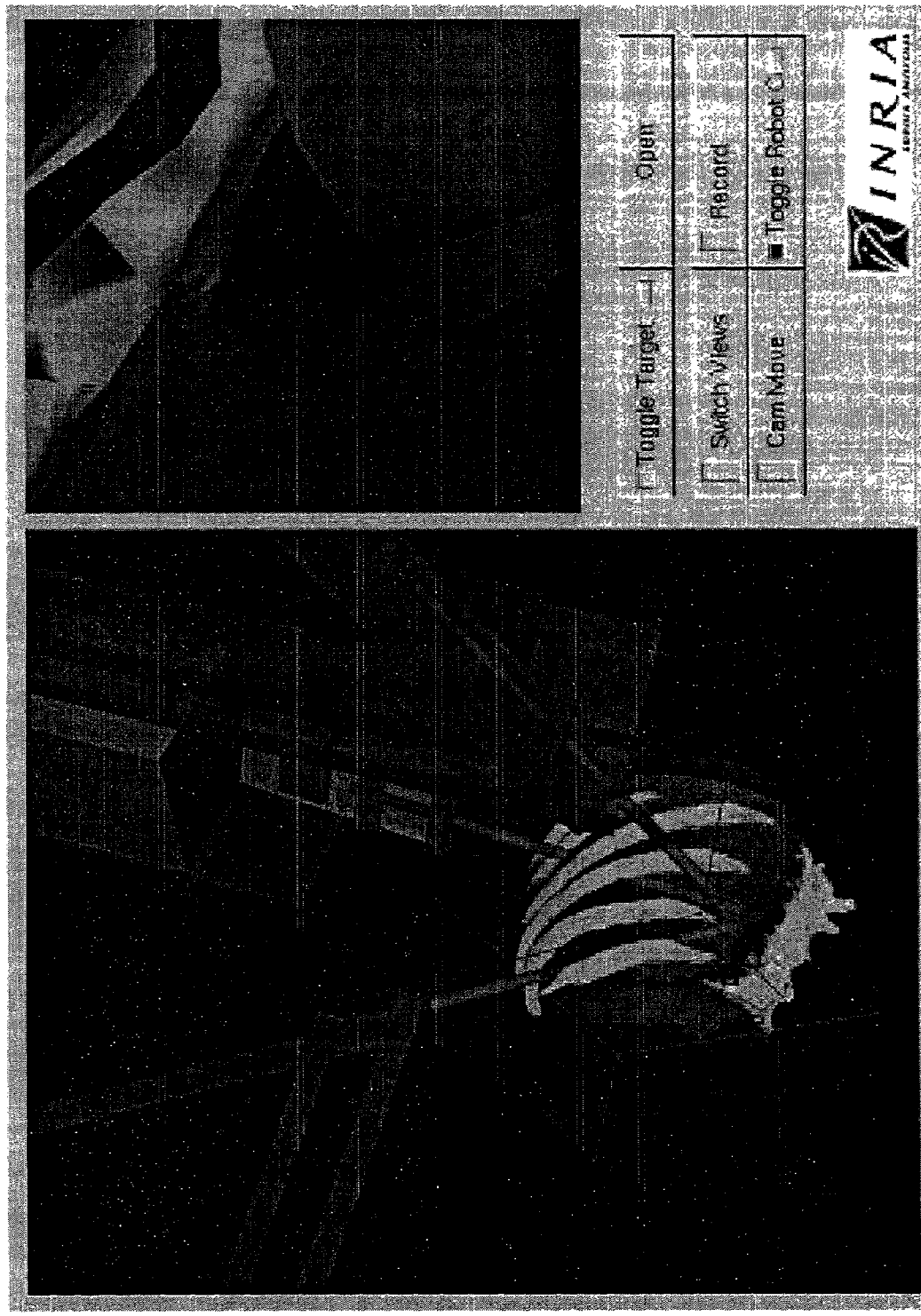
FIG. 8b is a screen shot perspective view of a computer interface for simulation of a surgical procedure according to an embodiment of the present invention.

FIGS. 8a and 8b show screen shots representing an embodiment of an apparatus for simulation 140 of a surgical procedure. FIG. 8a is a screen shot side view of a computer interface for simulation of a TECAB procedure. The interface may allow a surgeon to manipulate the computerized view of the simulation, to view the simulation from other angles, for example. FIG. 8b is a similar screen shot perspective view of a computer interface for simulation of a TECAB procedure.

Again referring to FIG. 3, once entry port placement and robot positioning have been validated 130 and simulated 140, they may be registered 150. Registration 150 generally refers to a process of transferring the entry port and robot placement from a simulator to an actual defined volume, such as a patient in an operating room ("OR"). In one embodiment, it is assumed that the robot base will be parallel to the OR table, and that the relative tilt between the skeleton used for simulation (or other simulation device) and the OR table is the same as the one in the CT scan. The translational pose is registered by identifying an particular point (such as the tip of the sternum) in the simulator using the endoscope, and reading the corresponding articular values. Then the robot base and its first translational joint (up/down) are moved so that the articular values read through an applications program interface (API) match the computed ones. Generally, an API is an interface including data from robot arm sensors, various other robot sensors, and the like, for registering robot positioning.

Once the robot is registered to the simulation skeleton, positioning the ports may simply be achieved by moving the robot arms according to the precomputed articular values that correspond to having the remote center on the port. On the other hand, the results of the planning can also be expressed as a quantitative description of the positions of the port, for example endoscope arm at third intercostal space at the limit of the cartilage. This is a relatively accurate description since the ports are planned to be located in the intercostal spacing. When entry port locations are identified and the robot is positioned, a surgeon or other operator may begin the procedure.

As described above, one embodiment of the present invention may be described as a method for surgical planning. The following is a more detailed description, set forth in a series of steps, of such an embodiment. Again, this description is provided for exemplary purposes only. In other embodiments, multiple steps may be added, eliminated, combined, performed in different orders, performed simultaneously, and/or the like, without departing from the scope of the invention. Therefore, the following description should not be interpreted to limit the scope of the invention as defined by the appended claims.

EXAMPLE METHOD

Step 1: Robotic system modeling. Step 1 typically includes defining a model of the insertable surgical tool portion, including structure, range of motion (ROM) limits, and optionally tool-type specific properties. Step 1 also includes defining a model of the external portion or robotic tool and manipulator arm structure and ROM limits. Finally, step 1 includes defining a multiple-arm robotic system model. Optionally, the model may include adjacent OR equipment such as operating table and accessories.

Step 2: Defining port feasibility criteria. Port feasibility may be defined, for example, relative to "reachability" criteria based on patient and tool models. Such criteria may include, for example: maximum acceptable port-to-target distance (i.e., tool shaft length, for endoscope, may include an objective lens offset); maximum acceptable entry angle, the angle between port-to-target path and the port direction—may depend on body wall properties, intercostal spacing, thickness, elasticity, etc., and may have different values in different body regions; determination that port-to-target path is clear of obstructions; and/or additional feasibility criteria (e.g., surgeon preference, procedure specific or tool-type specific criteria).

Step 3: Defining port optimization criteria. Examples of criteria include: tool-to-target attack angle for each port; dexterity parameter; tool 1 to endoscope angle; tool 2 to endoscope angle; symmetry and alignment of Tool 1 and Tool 2 about Endoscope; port-to-port separation distance; and/or additional optimization criteria (e.g., surgeon preference, procedure specific or tool-type specific criteria).

Step 4: Defining port optimization algorithm. For example, a cost function may be defined, wherein the function value is determined by weighted criteria values.

Step 5: Defining collision/interference prediction algorithms. Step 5 involves, for example, defining collision and interference prediction/detection algorithms relative to robotic system and/or patient models. Examples of such algorithms may include: internal tool-tool and/or tool-organ collisions; external arm-arm, arm-equipment and/or arm-patient collisions.

Step 6: Defining operative motion prediction algorithms. This step involves defining a predictive model of expected range of surgeon-commanded operational tool movements during surgical task (generic task, specific procedural and/or tool-types).

Step 7: Modeling the patient. Various exemplary embodiments include the use of patient-specific data to characterize the body portion being treated. In some embodiments and surgical procedures, port optimization planning on a representative sample of patients will have sufficient generality to be useful as a generic port placement plan. Modeling a patient may involve several sub-steps, such as:
1. acquiring patient-specific data for at least a portion of patent's body via such modalities as CT, MRI, and or arterial angiograms;
2. segmenting acquired data to distinguish organ, bone, vessel and other tissue structures (may be automated, manual or a combination of these);
3. reconstructing segmented, acquired data to construct a 3D model for at least a portion of patent's body. Optionally, such a model may include additional overlaid patient data, a body cavity insufflation space model, and/or the like.

Step 8: Defining target criteria. Step 8 includes defining one or more surgical target points (e.g., location in the body of a particular intended tissue manipulation) and target direction (s) in relation to patient model, (the direction(s) most convenient for performing the surgical task, e.g., normal to an organ surface or a preferred direction relative to an organ structure). Target directions may be different for endoscope and each tool. A process model of the interventional surgical procedure may be defined, specifying one or more relevant surgical targets.

Step 9: Defining admissible port set. This step involves defining a set of admissible ports for target and/or surgical procedure in relation to patient model, includes the entry point location and normal direction for each port. The choice of the admissible locations set stems from the characteristics of the intervention and/or anatomy of the patient, and is meant to cover all possible entry points from which optimal ports are to be chosen. Determining this set can either be done empirically or automatically using specialized segmentation algorithms.

Step 10: Determining feasible port set. This step includes calculating port feasibility criteria for each admissible port, testing port feasibility, and eliminating failed ports.

Step 11: Determining optimized multiple-port combination. Step 11 may include applying an optimization algorithm to calculated optimization criteria for all feasible port combinations of the total arm number (e.g., all feasible 3-port combinations or triplets). Step 11 may also include adding more ports than arms for surgeon assistance (e.g. cardiac stabilizer). The total number of ports is often referred to as n-tuplet. Several ports may be chosen for the same arm (e.g. two different non-simultaneous positions of the endoscope). Alternatively, step 11 may include pre-selecting an endoscope port, and then optimizing other ports by considering all combinations of remaining feasible ports (in example below, remaining feasible port pairs), as in the following sub-steps:
1. optimizing endoscope port., e.g., selecting port for port-to-target path close to target direction;
2. optional port pair feasibility criteria, e.g., eliminating port pairs with less than a minimum port surface separation, to simplify optimization by avoiding highly probable internal and external collisions, and/or aberrant ports with regard to dexterity and/or visibility; and
3. optimizing tool(s) and/or endoscope(s) combinations. For 1 endoscope+2 tools, each combination is commonly referred to as a triplet. More generally, for 1 endoscope +n−1 tools, each combination is referred to as an n-tuplet. Note that the combination may include more than one endoscope, or an integrated multifunctional endoscope/tool. This step may include, for example., calculating the optimization criteria for each port combination; calculating cost function value; ranking the n-tuplet by cost function value; and selecting the n-tuplet which has the best cost function value.

Step 12: Determining an advantageous robotic system pre-surgical set-up configuration. Although the robotic system pre-surgical set-up position(s) may be determined empirically, preferably optimization methods are employed according to the principals of the invention. This may include determining positions for a portion or all of the "passive" flexibility degrees of freedom (dofs) of the system (i.e., "passive" in the sense of fixed during surgical treatment manipulation), including the base support position(s), base support orientation(s), set-up joint position(s), and the like. Note that different robotic surgical systems vary considerably in the number of passive pre-surgical set-up dofs. An exemplary process (e.g., probabilistic and gradient descent) may include:
1. defining a set of constraints on the system based on port location and/or trajectory modeling the intervention;
2. defining a cost function based on a measure of goodness including, e.g., separation between the arms; separation from obstacles; maximizing dexterity and/or maneuverability at the end effector(s);
3. running probabilistic optimization to get a set of admissible (constraints realized) solutions (position/orientation of the base and/or values for set-up joints); and/or
4. running gradient descent optimization from the above initial solutions to optimize measure of goodness.

Step 13: Performing validation. The validation step involves applying the predictive model of expected surgeon-commanded operational instrument movements for a surgical procedure during manipulations at a surgical target site within the body. (e.g., the range of motions of instrument end effector, wrist and shaft within the body cavity relative to the body model; the range of motions of robotic arms outside the body relative to system model and/or body model). Collision prediction algorithms are also applied to determine if collisions will occur.

Step 14: Re-selecting ports based on validation. If port placements and/or robot positioning fail the validation step, the port/positioning combination is rejected and steps 11 through 13 are repeated to choose new port placement locations and/or robot positions.

Step 15: Simulating surgical procedure. Step 15 involves performing interactive surgery rehearsal by the surgeon, including surgeon inputs for simulated robotic manipulations, applying collision prediction algorithms, and/or inputting surgeon subjective assessment of effectiveness.

Step 16: Re-selecting ports based on simulation. If simulation is unsatisfactory, port placements and/or robot positioning may be rejected and steps 11 through 15 may be repeated to select and validate new placements and/or positions. Optionally, if simulation is unsatisfactory, the surgeon may fix one or more of current ports, and/or pre-select one or more ports, based on simulation/rehearsal experience (e.g., A desirable tool or endoscope port), and repeat steps 11-15 to re-optimize with reduced feasible port set.

Step 17: Recording and analyzing simulation data. Recorded simulation history and computer data, including surgeon inputs, tool motions and robotic arm movements, may be used to refine models, optimization criteria, feasibility criteria and/or cost function terms.

Step 18: Repeating steps 8-17 for additional targets. For complex or multi-site procedures, planning steps may be repeated for all necessary surgical targets.

Step 19: Determining multi-target optimized robotic system base support position.

Optionally, method steps may be employed to optimize the base position of a robotic system to permit advantageous access to all targets. Preferably, the robotic system base support(s) are pre-positioned so that the multi-target procedure may be performed with no re-positioning of base support(s).

Step 20: Multi-target port optimization. Optionally, method steps may be used to re-optimize port triplets to use particular ports for more than one target (minimize total number of ports and reduce set up time when accessing multiple targets).

Step 21: Transferring and registering planning results to patient body and surgical system. For both robotic and non-robotic surgical procedures, the results of planning are transferred to the patient. The model of the planned procedure may be registered to the patient's body in the operating room. Transfer and registration may include the marking of port locations, and reproducing the planned initial positions and alignment of the instruments and/or robotic arms. For example, the following sub-steps may be used:

1. selecting common reference point(s) and/or directional bearing for patient on operating table and for models (robotic and patient models);
2. superimposing alignment of models to patient coordinates;
3. aligning the robotic system to the reference point(s) and bearings;
4. determining actual port locations based on model relative to patient coordinates; and
5. making incisions at determined port locations for instrument insertion.

Optionally, a robotic control system, joint position sensors and encoders may be employed to effect a transformation from patient reference coordinates to joint-space coordinates for the robotic system. In one embodiment, for example, a robotic arm may be positioned to touch one or more reference point(s) on the body surface. Robotic system coordinates may then be defined relative to the body reference point(s). Finally, joint position sensors may monitor the arm motions relative to the body reference point(s), to direct and/or confirm setup arm positioning according to the optimized procedure plan, and to direct and/or confirm instrument orientation and tip location to touch the body surface at a modeled port location and orientation.

Step 22: Collision detection during surgical procedure. Optionally, the collision prediction/detection algorithms may be applied to real-time robotic arm and instrument positions and orientations to predict, warn of, and/or avoid collisions during the procedure.

Step 23: Recording and analyzing operational data. Recorded procedure history and computer data, including surgeon inputs, tool motions and robotic arm movements, may be used to refine models, optimization criteria, feasibility criteria and/or cost function terms. The robotic surgical system may be provided with an Application Program Interface (API), or the equivalent, in communication with the robotic control system and/or endoscope imaging system, to permit recordation during the course of a surgical procedure (and/or real-time analysis) of sensor signals, encoder signals, motions, torques, power levels, rates, input commands, endoscope display images, and the like.

While the above is a complete description of exemplary embodiments of the invention, various alternatives, modifications and equivalents may be used. For example, various steps or stages in any of the above methods may be combined. For example, in one embodiment the planning and validation steps may be combined. In other embodiments, steps may be added or eliminated.

As described variously above, methods and apparatus of the present invention are not limited to robotic surgery, but may be applied to laparoscopic, minimally invasive, or other types of surgery. Furthermore, the present invention is not limited to any particular type or category of surgical procedure. Examples of surgical procedures (including veterinary surgical procedures) in which embodiments of the invention may be used include, but are not limited to robotic and non-robotic thoracic, abdominal, neurological, orthopedic, gynecological, urological surgical procedures, and/or the like. The surgical instruments and instrument combinations employed may include more than one endoscope, or may include an integrated multifunctional endoscope/tool. Likewise the instrument combinations may include interventional instruments used with or monitored by other modalities of medical imagery instead of, or in addition to, visual endoscopy, e.g., ultrasound, real-time MRI, CT, fluoroscopy, and the like When applied to robotic surgery, embodiments having aspects of the invention are not limited to any particular make or type of robotic surgical system. Thus, methods and apparatus according to the principles of the invention may include robotic systems having more or fewer than three robotic arms, surgical procedures employing two or more cooperative robotic systems, robotic surgical systems co-operated by two or more surgeons simultaneously, or the like. Embodiments having aspects of the invention may include surgical systems having passive center-of-motion robotic manipulators, computed center-of-motion robotic manipulators, and/or mechanically constrained remote center-of-motion robotic manipulators, and the like. Models of robotic systems employed in simulation and planning steps may include modeling of active manipulator links and joints (servo-operated and passively responding joints which move during tissue treatment operation). Robotic arm models may also include base support links and joints (set up or pre-positioning arms fixed during tissue treatment operation). Multiple-arm robotic systems employed in embodiments having aspects of the invention may include a plurality of robotic arms may have a single integrated support base (e.g., a multi-arm cart-type support base), or each arm may have an individual base (e.g., wherein each robotic arm is individually clamped to an operating table structure or rail), or combinations of these.

Additionally, the present invention is not limited to surgical procedures on a human patient or animal patient, but may be employed in a variety of non-surgical or quasi-surgical procedures and operations. The principles of the invention are particularly suitable to operations usefully performed by remotely operated or robotic tools, where substantially similar modeling, planning and simulation methods are useful. Examples include operations on a defined target volume, such as deactivation of a suspected explosive device; remote inspection and operations within a container, vehicle, or the like; underwater operations; and rescue operations in a collapsed structures, mine and the like. In non-surgical and quasi-surgical target volumes, the modeling of the target volume may optionally be based, at least in part, on archival data, such as engineering data, architectural data, CAD file inputs, and the like, as well as a variety of different actively acquired data modalities.

Therefore, the above description should not be taken as limiting the scope of the invention which is defined by the appended claims.

What is claimed is:

1. A method for simulating a robotic surgical procedure on a computer, the method comprising:
   identifying a plurality of port optimization criteria;
   assigning numerical values to the port optimization criteria associated with each of at least two candidate port arrangements;
   computing a cost metric for each candidate port arrangement, the cost metric comprising a weighted combination of the numerical values assigned to the port optimization criteria for that candidate port arrangement;
   selecting the candidate port arrangement having an optimal value of the cost metric; and
   simulating a robotic surgical procedure on a human body with the selected candidate port arrangement as the arrangement of a plurality of surgical entry ports in the human body.

2. The method as in claim 1, wherein the plurality of criteria includes at least one of robot kinematics, robot kinetics, robot work range, deviation of tool entry angle from normal, organ geometry, surgeon defined constraints, robot force limitations, and patient force limitations.

3. The method as in claim 1, wherein the plurality of criteria includes at least one of a deviation from a desired configuration, arm placement symmetry with respect to endoscope positioning, and tool entry angle with respect to surface normal.

4. The method as in claim 1, the assigning numerical values comprising employing imaging data acquired using at least one of computed tomography, magnetic resonance imaging, conventional radiography, and arterial angiography.

5. The method as in claim 1, further comprising determining positions for robotic arms individually holding one of a triplet of medical devices for insertion into three surgical entry ports.

6. The method as in claim 5, wherein the determination of the positions of the robotic arms is based at least in part on a set of criteria, the criteria including at least one of robot kinematics, robot kinetics, robot work range, deviation of tool entry angle from normal, organ geometry, surgeon defined constraints, robot force limitations, and patient force limitations.

7. The method as in claim 1, further comprising: preparing a representation of a defined volume within the patient from a set of acquired data; and facilitating a first simulation for enabling a user to simulate a medical procedure performed through said surgical entry ports, the first simulation based upon the representation of the defined volume, the advantageous locations of the entry ports, and a surgical protocol.

8. The method as in claim 7, further comprising:
   enabling the user to reject one or more of the advantageous locations based on the first simulation;
   determining different advantageous locations based on the user's rejection; and
   facilitating a second simulation for enabling the user to simulate the medical procedure, the second simulation being based upon the model of the defined volume, the different advantageous locations of the entry ports, and the surgical protocol.

9. The method as in claim 1, further comprising storing information of the advantageous locations in a memory.

10. An apparatus for simulation of a robotic surgical procedure, the apparatus comprising a tangible medium configured with machine readable code to:
    identify a plurality of port optimization criteria;
    assign numerical values to the port optimization criteria associated with each of at least two candidate port arrangements;
    compute a cost metric for each candidate port arrangement, the cost metric comprising a weighted combination of the numerical values assigned to the port optimization criteria for that candidate port arrangement; and
    select the candidate port arrangement having an optimal value of the cost metric;
    wherein the machine readable code is further configured to facilitate simulation of a robotic surgical procedure on a human body with the selected candidate port arrangement as the arrangement of a plurality of surgical entry ports in the human body.

11. The apparatus as in claim 10, wherein the machine readable code is further configured to determine a preferred position for placement of a robotic apparatus relative to the plurality of surgical entry ports.

12. The apparatus as in claim 10, wherein the plurality of criteria includes at least one of robot kinematics, robot kinetics, robot work range, deviation of tool entry angle from normal, organ geometry, surgeon defined constraints, robot force limitations, and patient force limitations.

13. The apparatus as in claim 10, wherein the plurality of criteria includes at least one of a deviation from a desired configuration, arm placement symmetry with respect to endoscope positioning, and tool entry angle with respect to surface normal.

14. The apparatus as in claim 10, the machine readable code configured to assign numerical values by employing imaging data acquired using at least one of computed tomography, magnetic resonance imaging, conventional radiography, and arterial angiography.

15. The apparatus as in claim 10, the machine readable code further configured to determine positions for robotic arms individually holding one of a triplet of medical devices for insertion into three surgical entry ports.

16. The apparatus as in claim 15, wherein the determination of the positions of the robotic arms is based at least in part on a set of criteria, the criteria including at least one of robot kinematics, robot kinetics, robot work range, deviation of tool entry angle from normal, organ geometry, surgeon defined constraints, robot force limitations, and patient force limitations.

17. The apparatus as in claim 10, the machine readable code further configured to:
prepare a representation of a defined volume within the patient from a set of acquired data; and
facilitate a first simulation for enabling a user to simulate a medical procedure performed through said surgical entry ports, the first simulation based upon the representation of the defined volume, the advantageous locations of the entry ports, and a surgical protocol.

18. The apparatus as in claim 17, the machine readable code further configured to:
enable the user to reject one or more of the advantageous locations based on the first simulation;
determine different advantageous locations based on the user's rejection; and
facilitate a second simulation for enabling the user to simulate the medical procedure, the second simulation being based upon the model of the defined volume, the different advantageous locations of the entry ports, and the surgical protocol.

19. The apparatus as in claim 10, the machine readable code further configured to store information of the advantageous locations in a memory.

20. A robotic surgical system comprising:
first and second robotic arms adapted to respectively hold first and second surgical tools for performing a medical procedure on a patient;
a third robotic arm adapted to hold an image capturing device, and
a computer for selecting a preferred arrangement of entry ports for the first and second robotic arms from among at least two candidate port arrangements, the computer configured to:
identify a plurality of port optimization criteria;
assign numerical values to the port optimization criteria associated with each candidate port arrangement;
compute a cost metric for each candidate port arrangement, the cost metric comprising a weighted combination of the numerical values assigned to the port optimization criteria for that candidate port arrangement;
select the candidate port arrangement having an optimal value of the cost metric as the preferred arrangement of the plurality of surgical entry ports;
wherein the computer is further configured to facilitate simulation of a robotic surgical procedure on the patient with the selected candidate port arrangement as the arrangement of a plurality of surgical entry ports in the patient.

21. The system of claim 20, wherein the computer further comprises a display device for displaying the simulation of the medical procedure.

22. The system as in claim 20, wherein the plurality of criteria includes at least one of robot kinematics, robot kinetics, robot work range, deviation of tool entry angle from normal, organ geometry, surgeon defined constraints, robot force limitations, and patient force limitations.

23. The system as in claim 20, wherein the plurality of criteria includes at least one of a deviation from a desired configuration, arm placement symmetry with respect to endoscope positioning, and tool entry angle with respect to surface normal.

24. The system as in claim 20, the computer configured to assign numerical values by employing imaging data acquired using at least one of computed tomography, magnetic resonance imaging, conventional radiography, and arterial angiography.

25. The system as in claim 20, the computer further configured to determine positions for robotic arms individually holding one of a triplet of medical devices for insertion into three surgical entry ports.

26. The system as in claim 25, wherein the determination of the positions of the robotic arms is based at least in part on a set of criteria, the criteria including at least one of robot kinematics, robot kinetics, robot work range, deviation of tool entry angle from normal, organ geometry, surgeon defined constraints, robot force limitations, and patient force limitations.

27. The system as in claim 20, the computer further configured to:
prepare a representation of a defined volume within the patient from a set of acquired data; and
facilitate a first simulation for enabling a user to simulate a medical procedure performed through said surgical entry ports, the first simulation based upon the representation of the defined volume, the advantageous locations of the entry ports, and a surgical protocol.

28. The system as in claim 27, the computer further configured to:
enable the user to reject one or more of the advantageous locations based on the first simulation;
determine different advantageous locations based on the user's rejection; and
facilitate a second simulation for enabling the user to simulate the medical procedure, the second simulation being based upon the model of the defined volume, the different advantageous locations of the entry ports, and the surgical protocol.

29. The system as in claim 20, the computer further configured to store information of the advantageous locations in a memory.

* * * * *